United States Patent [19]

Jennings

[11] Patent Number: 5,065,634
[45] Date of Patent: Nov. 19, 1991

[54] METHOD AND APPARATUS FOR THE AUTOMATIC DETERMINATION OF SURFACE AREA

[76] Inventor: Howard Jennings, 42 Pinetree La., Roslyn Heights, N.Y. 11577

[21] Appl. No.: 580,142

[22] Filed: Sep. 10, 1990

[51] Int. Cl.$^5$ ............................................. G01N 15/08
[52] U.S. Cl. ................................................. 73/865.5
[58] Field of Search ...................... 73/1 G, 866, 28.01, 73/865.5

[56] References Cited

U.S. PATENT DOCUMENTS

| | | | |
|---|---|---|---|
| 2,960,870 | 11/1960 | Nelsen et al. | 73/28.01 |
| 3,555,912 | 1/1971 | Lowell | 73/865.5 |
| 3,884,083 | 5/1975 | Lowell | 73/865.5 |

Primary Examiner—Robert Raevis
Attorney, Agent, or Firm—Collard, Roe & Galgano

[57] ABSTRACT

A method for determining the surface area of a material by using the dynamic flow method, by continuously passing a stream of a gaseous mixture of known and constant composition consisting of an adsorbate such as nitrogen and an inert gaseous diluent such as helium in contact at a constant pressure with a measured sample of the material at a temperature at which neither the inert diluent nor the adsorbate is appreciably adsorbed by the sample. Then, while continuing said stream, the sample is cooled to a temperature at which adsorption of the adsorbate by the sample selectively takes place. Using a detector, one continuously measures the decrease in the concentration of the adsorbate in the stream, down stream of the sample, during the cooling and until equilibrium is re-established. By using a sensing circuit, one integrates the measured decrease in concentration of the adsorbate over the period of cooling until the equilibrium is re-established. A gate circuit is used to inhibit all signals emanating from the detector immediately after the sample is immersed in the gaseous mixture, to eliminate false or phantom signals generated in the detector by the chilling of the gas mixture. The inhibit gate is then deactivated to reconnect the detector to the sensing or readout circuit so that the completion of the adsorption signal can be detected. The liquid nitrogen bath is then lowered or removed from the sample of material in response to the absorption completion signal to cause the sample of material to warm to ambient temperature, and permit desorption of the adsorpted nitrogen in the sample of material. The desorbed nitrogen from the sample of material is detected by the detectors, so as to generate a signal proportional to the volume of nitrogen adsorbed by the sample of material, so as to provide a measure of the surface area of the sample of material.

10 Claims, 3 Drawing Sheets

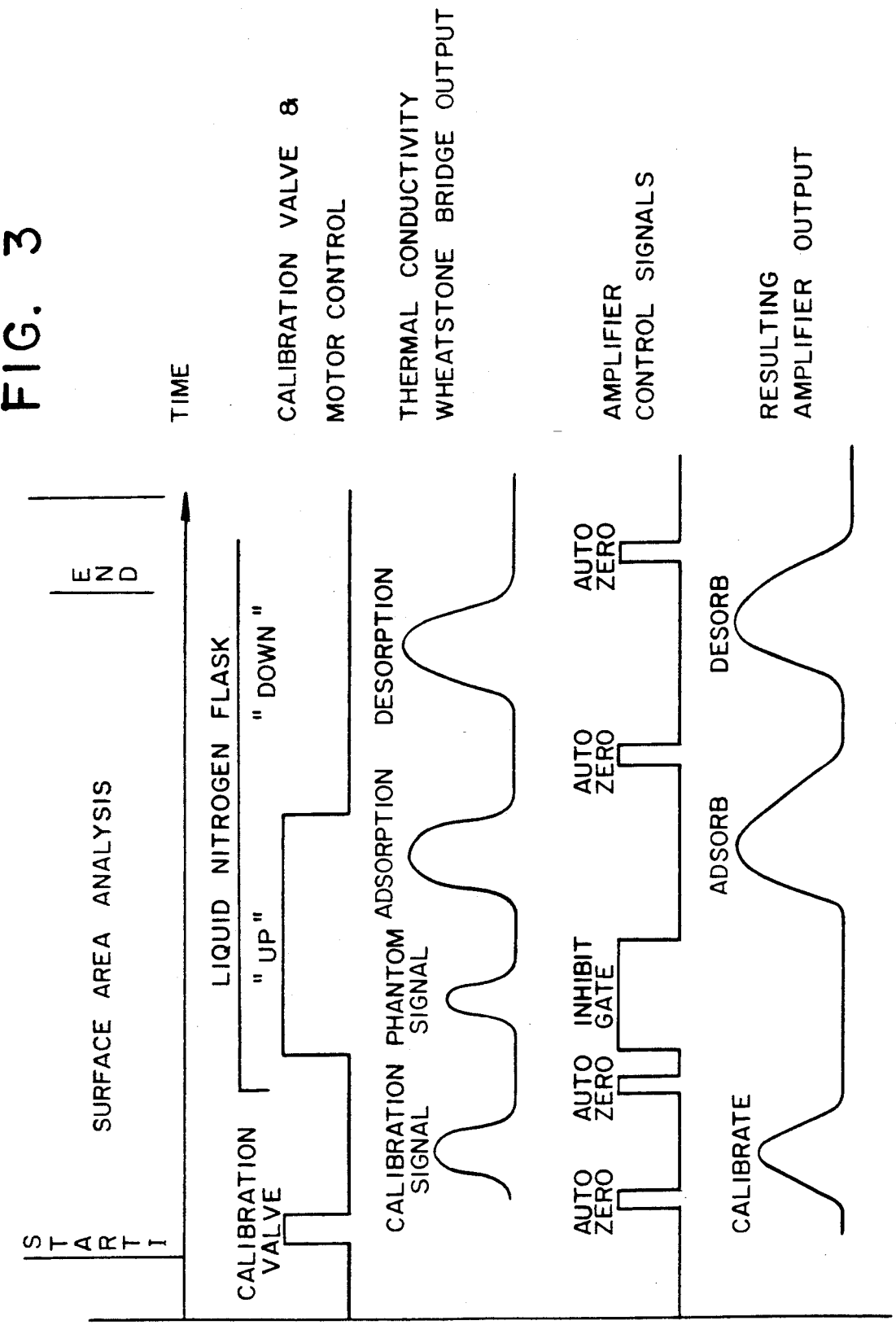

METHOD AND APPARATUS FOR THE AUTOMATIC DETERMINATION OF SURFACE AREA

BACKGROUND OF THE INVENTION

1. Field of the Invention

This invention relates to a method and apparatus for the surface area determination of solids that is free from operator bias and produces reliable results.

2. Discussion of the Prior Art

Various prior art methods have been used to determine the surface areas of solids. The most effective and commonly used is the method of S. Brunauer, P. H. Emmett and E. Teller described in the J.Am.Chem.Soc. 60,309 (1938). This method, commonly referred to as the BET method, involves the determination of the volume of adsorbate gas (usually nitrogen) adsorbed, then desorbed by a sample at relative pressures below 0.35 psi. The BET method was later improved by the U.S Bureau of Standards. (See W. V. Loebenstein and V. R. Dietz) J. Research Natl. Bur. Standards, vol. 46, No. 1, pp 51-53 (1951).

The invention of Fred M. Nelsen and Frank T. Eggertsen, U.S. Pat. No. 2,960,870, was the first apparatus and method that was faster and simpler than the old vacuum systems it replaced, but was still limited in acceptance because it was too slow to effectively monitor on-going processes in factories that were trying to measure and control the surface area of their products. The instrument required skilled operators who were familiar with gas chromatographic techniques. However, their instrument (the Shell Sorptometer) was the first embodiment of the BET method to result in a practical instrument that was accurate, and applicable over a wide range of surface areas. Most importantly, the Shell device provided an improved method of calibration which presented direct read-out of surface area without resorting to reference materials. (See Section 5, lines 36 to 43 and lines 51 and 52 of U.S. Pat. No. 2,960,870.)

In general, the Nelsen and Eggertsen "Shell Sorptometer" utilized gas chromatographic techniques, in what has become known as the dynamic flow system, to deliver the adsorbate nitrogen, at relative pressures below 0.35 psi. to the sample. The sample was then cooled in liquid nitrogen, and the volume of nitrogen adsorbed, then desorbed by the sample was determined by integration of the signals obtained from the thermal conductivity bridge. The Shell Sorptometer required the precise and frequent injection of known volumes of nitrogen (by syringe) in order to keep the unit in calibration. The detectors were run at elevated temperatures, and were very sensitive to changing ambient conditions. As a result, it was essential to constantly balance, or null the wheatstone bridge detecting circuits comprised by these thermal conductivity detectors.

All dynamic flow instruments are subject to the variations in null point caused by temperature variations of the flowing gas stream at the onset of the adsorption cycle when the sample, and the gas mixture flowing through it are immersed in liquid nitrogen. These fluctuations produce "phantom" signals which are so similar to "true" adsorption signals that they will be misread by the logic and command circuits of an automatic surface area analyzer which will then respond in an inappropriate manner; for example, the "phantom" signal will be thought to be the adsorption signal, and when it (the "phantom" ends, and the detector returns to null, the logic circuitry will read that as the completion of the adsorption cycle, which has not yet begun, and lower the bath of liquid nitrogen, to permit the desorption process to begin.

To counter these fluctuations in the detector caused by these temperature changes, efforts were made to make the detector immune to these temperature changes. The detectors were immersed in a constant temperature bath (see U.S. Pat. No. 2,960,870 lines 4-18 to 4-21), or more recently in proportionally controlled ovens such as used in the Flowsorb 2300 (manufactured by Micromeritics Corporation, Norcross, Ga. These attempts to control the temperature of the detector to avoid the drift and fluctuations caused by the shifting temperature of the gas mixture, compromised the reliability and serviceability of these instruments and still required the operator to readjust two bridge balance controls throughout the entire analysis.

BRIEF DISCUSSION OF THE INVENTION

An object of this invention is to eliminate the effects caused by these temperature fluctuations, not by wasting heater power to counter the temperature changes, but simply to disconnect the detector from the instrument amplifiers and logic and control circuits during these transitional periods. This is accomplished in a unique application where an analog switch is used as an inhibiting circuit, or "gate" which is commanded by logic circuits. These logic circuits order the "gate" to be closed to all signals emanating from the thermal conductivity detector in the interval of time (typically 60 to 90 seconds) immediately after the sample is immersed in liquid nitrogen. In this way the "phantom" signals are permitted to run their course without expending any effort to oppose or neutralize their effect; they are simply ignored.

In the present invention, the gate is always activated when operating in the automatic mode when the instrument functions without an operator in attendance. The gate is deactivated in the manual mode which is only used to establish the initial conditions when the instrument is first turned on. This invention also eliminates all bridge balancing controls currently used by every prior art dynamic flow surface area analyzer being manufactured.

These required interventions by the operator on prior art equipment made truly automatic operation of these instrument impossible. They also compromised the reproducability of the measurement because different operators would arrive at different "balance conditions" using the same controls and indicating meters. In fact, the same operator would introduce random scatter in the data being used for process control because of his inability to repeat the balance conditions from analysis to analysis. Since the skill and diligence of the operators of the instrument differed widely, operator bias has been a significant source of error in the measurements. Repeatability, essential in such an instrument, was therefore degraded.

Other objects and features of the present invention will become apparent from the following detailed description considered in connection with the accompanying drawings which disclose the embodiments of the invention. It is to be understood however that the drawings are designed for the purpose of illustration only and not as a definition of the limits of the invention.

In the drawings wherein similar reference characters denote similar elements throughout the views:

FIG. 3 discloses the control signals and detector waveforms of the circuit of FIG. 2.

Figure 1:
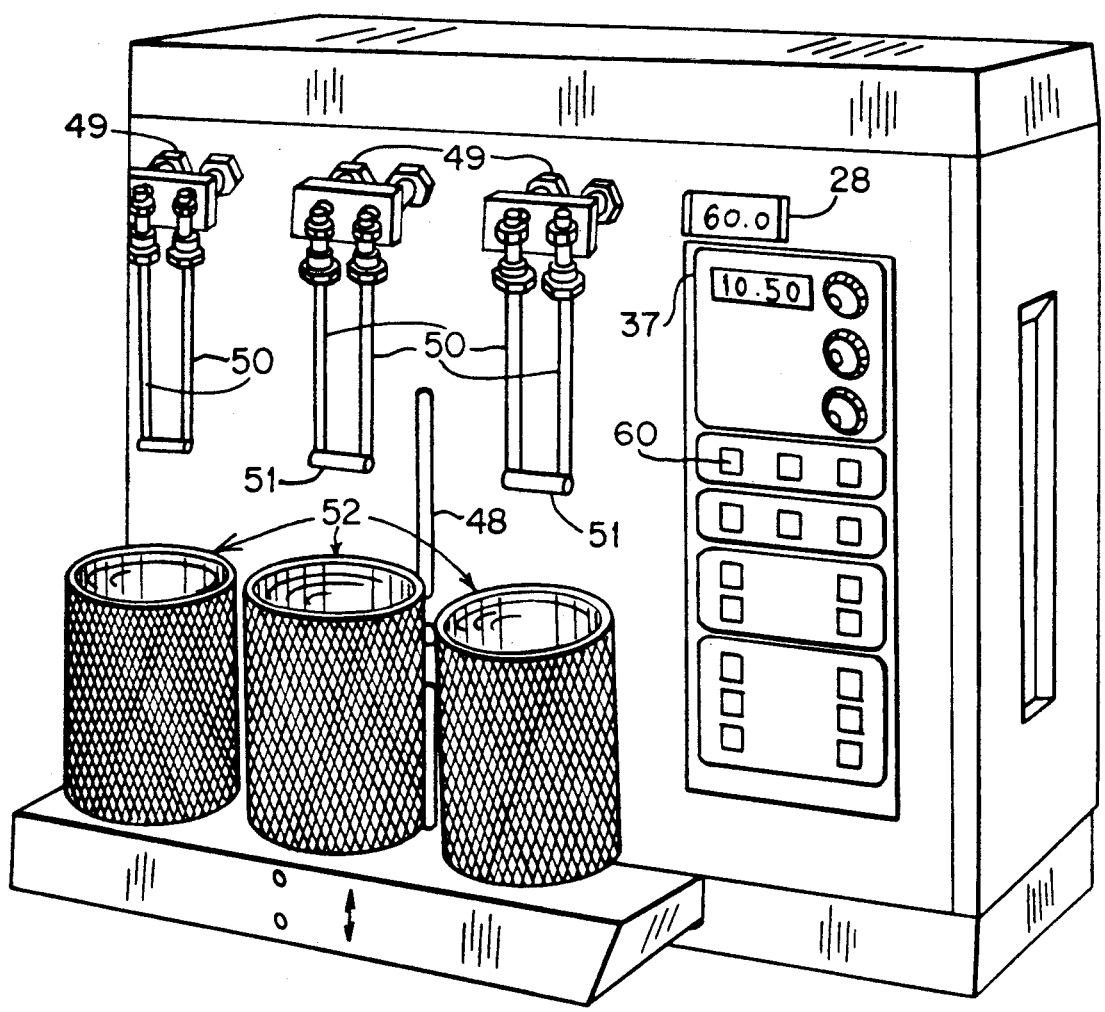
FIG. 1 is a perspective view of the improved surface area analyzer of the subject invention.
Figure 2:
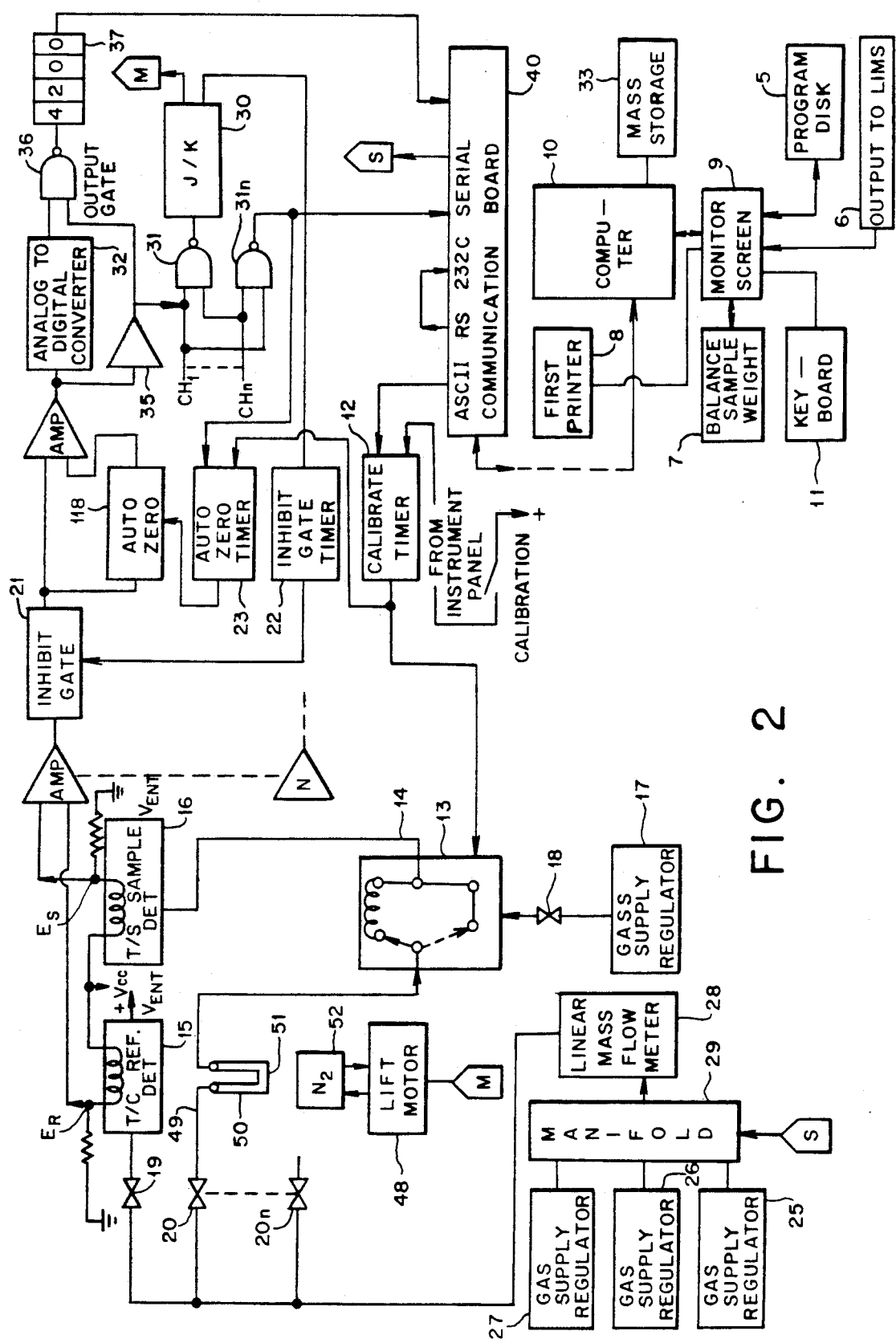
FIG. 2 is a block diagram partly in schematic form of the surface area analyzer of FIG. 1.

Referring to FIGS. 1-3, there is shown the surface area analyzer of the present invention capable of performing surface area measurements on raw materials, finished goods and experimental products.

Surface area measurements are made in dynamic flow instruments (such as described in U.S. Pat. No. 2,960,870, to Nelsen) in the following way.

A 30% nitrogen balance helium gas mixture is made to flow along line 49 through the powder sample 51 held in U-shaped tube 50. The sample in U-tube 50 is then immersed in a bath of liquid nitrogen 52, which is moved upward by lift motor 48 into position to surround glass tube 50. This causes the nitrogen gas in the mixture of line 49 to be adsorbed by sample 51. When the sample has adsorbed all the nitrogen it can, it is returned to room temperature by lowering bath 52, and the adsorbed nitrogen is desorbed. The desorbed volume is measured by the instrument, as described below. The BET equation states that every cubic centimeter of nitrogen adsorbed by a sample from a 30 percent mixture at liquid nitrogen temperature is equivalent to a surface area of 2.84 square meters.

The purpose of this invention, in part, is to measure the volume of nitrogen adsorbed, then desorbed from a flowing gas mixture and apply the BET equation to determine the surface area equivalent. The instrument does this in the steps outlined below:

A mixture of nitrogen as adsorbate and helium, the inert carrier, are selected. The mixture must be in the (relative pressure) range of 0.05 to 0.35 ratio nitrogen to helium. In this invention, this selection is made when the operator is prompted by a message on PC monitor screen 9 to "Select Mixture". A mixture can be selected by the PC computer, of either 10 percent, 20 percent or 30 percent of nitrogen balanced helium mixture, by selection of gas mixture from one of regulators 25, 26 and 27 that feed manifold 29, which is connected to RS-232c serial board 40. A linear mass flow meter 28 couples manifold 29 to valve 20. The use of a linear mass flow meter with digital display permits the actual flow rate to be monitored at the computer and by setting upper and lower permissible limits be used to warn the operator of the changed conditions. Also, by extension, it would be possible to use this information to automatically compensate for any small change in flow rate. This is all new and novel because older units use simple rotameter floats in a glass column to indicate flow rate and they do not permit feedback and control. For the purposes of illustration, a 30 percent $N_2$/Bal helium mixture at a constant flow rate is established by needle valve 19 for each channel from CH #1, CH #2 . . . to CH #N. The needle valve establishes the flow rate in a detector 15. The voltage developed across this detector element is a function of the thermal conductivity of the gas mixture and the flow rate. Both are held constant throughout the analysis; therefore, the voltage $E_R$ remains constant throughout analysis.

The mixture (30 percent) also flows through the sample cell 50 for each channel. This glass cell contains sample 51 to be analyzed. After flowing through cell 50, the mixture flows through calibration valve 13, and then to sample detector 16 for Channel #1. Calibration loop 14 is always filled to capacity, with 1 cc of pure nitrogen calibration gas from source 17, at a flow rate controlled by needle valve 18.

The initial conditions for setting up the test are as follows:

In the beginning with an identical gas mixture of 30 percent flowing through both detector 15 and Channel #1, sample detector 16, the voltages $E_R$ and $E_S$ would be equal if all circuit elements were identical. Since these elements are not always equal, the invention provides an automatic zeroing circuit 118.

To begin the analysis, when the instrument is used with a computer 10, then the software 8 is loaded into computer 10, and instructions appear on the monitor screen 9 directing the operator on keyboard 11, for example, to enter the name of the sample and the weight of the sample. Then the operator is prompted to press "R" to run the analysis. Computer 10 is also connected to a printer 8, and a balance 7 for weighing samples. When operator presses "R" on keyboard 11, this command activates calibration timer 12.

Calibration timer 12 drives calibration valve 13, which injects the contents of the calibration loop 14 into the flowing gas mixture (30 percent) flowing from the channel #1 sample cell 50. The sample loop 14 contains 1 cc. of nitrogen gas from source 17 (see also FIG. 3).

When the flowing stream, which now contains 1 cc of pure nitrogen, is swept through sample detector 16, the detector reacts to the increase in nitrogen in the mixture. The detector's temperature changes and causes a change in the current through it. This causes a change in the voltage $E_S$. The changed voltage, $E_S$ will disturb the balance (or zero condition that existed with the reference voltage $E_R$) during the time it takes for this nitrogen "rich" gas mixture to be swept through detector 16. When injected volume completes its passage through detector 16, the balance or zero condition is re-established in balance circuit 7.

The "signal" caused by the calibration volume of 1 cc. being swept through detector 16 is integrated and stored on the instrument panel display and on computer screen 9 and in computer memory 10. Its value is directly proportional to the 1 cc volume of $N_2$ calibration gas.

The sequence gate 31 detects the completion of the calibration signal and instructs the sequence controller 30 (a J/K flip-flop) to:

(a) Activate the LIFT MOTOR M, and raise the bath of LIQUID nitrogen.

(b) Activate the INHIBIT gate circuit 21 to DISCONNECT amplifier and integrator circuits from the (Difference Voltage) signal which exists between voltage $E_R$ and $E_S$, for approximately 60 seconds using gate timer 22. This avoids the false or "phantom" signals generated in sample detector 16 by the CHILLING of the gas mixture when it initially flows through sample 51 immersed in liquid nitrogen. All prior art devices required constant temperature baths for sample detector 16, and constant adjustment of balance/zero controls by the operator to counter this problem. The present inventive approach simply "inhibits" or disconnects the signal from the amplifier during that transition period for the first 60 seconds after the sample is immersed in nitrogen. Thereafter, the deactivated inhibit gate 21 permits normal processing of adsorption and desorption signals.

Inhibit circuit 21 is activated as follows:

When sequence controller 30 orders the bath of liquid nitrogen 52 to be raised by motor 48, it also activates "inhibit gate timer" 22. This inhibit gate timer 22 closes inhibit gate 21 for the first 60 seconds after bath of liquid nitrogen is raised. This eliminates the need to control or neutralize the effects of gas temperature changes on the thermal conductivity detectors by closing "gate" circuits between the detectors and instrumentation amplifiers during the first 60 to 90 seconds after the immersion of the sample cell (and sample) in the liquid nitrogen bath. This gate closing or inhibiting circuit permits the "phantom" signals to run their course, and then the detector is reconnected (the gate is opened) to the instrumentation amplifiers and the analysis continues to its completion. Then the gate is opened again to process the adsorption signal. The adsorption signal is generated when the nitrogen in the gas mixture flowing through the sample in cell 50, which is immersed in liquid nitrogen, changes from its gaseous state. The nitrogen in the mixture becomes liquid like at the liquid nitrogen temperature and becomes adsorbed in the pores of sample 51. The helium carrier in the mixture is unaffected by this liquid nitrogen temperature.

Sample detector 16 will begin to respond to the change in nitrogen content of the gas mixture. Since there now is much less nitrogen, the temperature of sample detector 16 will change and produce a change in voltage $E_S$. This change with respect to the voltage at the reference detector $E_R$ generates a signal which is integrated by the analog to digital converter 32 and stored in the computer storage 33 as "adsorbed" data. The integrated value is a function of the volume of nitrogen adsorbed. Analog to digital converter 32 includes threshold detector 35, and feeds it output via output gate 36 and surface area display 37 to RS-32c board 40, connected to computer 10.

Sequence gate 31 detects the completion of the adsorption signal and instructs the sequence controller 30 to: (a) drive motor 48 to lower bath 52 of liquid nitrogen; (b) send data to computer 10; and, (c) actuate auto zero timer 23 to recheck and adjust if necessary "zero" condition between reference voltage, $E_R$ and sample voltage $E_S$.

When sample cell 50 is removed from liquid nitrogen bath 52, it warms back to room temperature. All of the liquid nitrogen that had been adsorbed by sample 51, now returns to its gaseous state and is swept by the flowing gas mixture into sample detector 16. Sample detector 16 now responds to a nitrogen rich signal, and its temperature, and the current through it, will change accordingly. This signal is integrated in analog to digital converter 32 and is sent to computer 10 for display and storage.

Sequence gate 31 detects completion of the desorption signal and ends the analysis. This information is sent to computer 10 which prompts the operator to enter the final weight of the sample, and responding, then calculates the BET surface area equivalent of the volume of nitrogen (adsorbed then) desorbed by the sample.

Surface Area Computation: The BET theory and equation which is used to measure the BET surface area of a material requires the following in simplified terms: measure the volume of nitrogen which is first adsorbed from a gas mixture of 30 percent (nitrogen, balance helium) and then desorbed. Each cubic centimeter of nitrogen adsorbed is equivalent to a. BET surface area of 2.84 square meters.

All dynamic flow instruments determine the volume of nitrogen gas (adsorbed then) desorbed from the sample simply by taking the ratio of the integrated values of the signals generated in the detectors by the calibration volume and desorbed volume of nitrogen. See below:

$V_C$ = Calibration Volume = 1 cc (given)
$V_D$ = Desorbed Volume, To be determined
$I_C$ = Integration of Calibration "signal"
$I_D$ = Integration of Desorbed "signal"

Therefore:

$$\frac{V_C}{I_C} = \frac{V_D}{I_D}$$

and solving for volume desorbed $$V_D = V_C \times \frac{I_D}{I_C}$$

$$V_D = 1 \text{ cc} \times \frac{I_D}{I_C}$$

Once the desorbed volume is known, it is divided by the factor $$\frac{2.84 \text{ square meters}}{\text{cc of desorbed gas}}$$

The following example illustrates that when the calibration volume of 1 cubic centimeter of nitrogen is injected into the flowing stream, it generates a signal such as shown below and the signal is integrated resulting in a digital display of 2.95 "counts".

Calibration Signal Integrated Value = 2.95 "counts"

Solving Equation Desorbed Volume = $V_D = V_C \times \frac{I_D}{I_C}$ $$V_D = 1 \text{ cc} \times \frac{5.90}{2.95}$$

$$V_D = 1 \text{ cc} \times 2 = 2 \text{ cc}$$

and since surface area = $\frac{2.84 \text{ square meters}}{\text{cc desorbed}}$ The surface area of sample in cell is:

$$\frac{(2.84 \text{ square meters})}{\text{cc}} \times 2 \text{ cc} = 5.68 \text{ square meters}$$

The self calibration and self-contained RS-232c communication port 40 combine to eliminate one of the most serious limitations of the prior art dynamic flow surface area instruments. This limitation is caused by the fact that if the flow rate does not remain constant, or if it changes between the operator's infrequent calibration syringe injections, then direct read-out of surface area will result in significant error.

In the present invention, the instrument is automatically calibrated at the beginning of each analysis, and any change in flow rate is immediately detected, its effect stored in memory and accounted for in the final computation of surface area. Changes in flow rate, therefore, have no effect on the accuracy of the analysis.

The automatic self-balancing thermal conductivity detector bridge circuits 15, 16 are uniquely designed to be self-nulling, and the sample and hold circuits are activated at the beginning of each sequence in the analysis, namely, at the beginning of the calibration, adsorption and desorption cycles. The circuits employ low leakage capacitors, operational amplifiers with low offset voltages, and a unique series connection of two elements of an analog switch which combine to hold the "zero" or balance condition for periods of time (30 to 45 minutes) longer than any portion of the analysis. This "zero" condition is reconfirmed four times during an analysis (see FIG. 3), which typically takes less than 10 minutes on this instrument.

The self-balancing circuits guarantee that any drift that might have taken place in the thermal conductivity wheatstone bridge detection circuits is canceled out and eliminated as a source of error in the analysis. This relieves the operator of the task of calculating the calibration constant for the gas mixture being used.

Moreover, selection of the gas mixture is available from the computer keyboard with the automatic calculation of the calibration factor appropriate to that gas mixture computed within the software. This feature permits multipoint BET analysis to be conducted, if desired.

The instrument automatically transmits the sample weight via serial communication port 40 on the analytical balance and assures that no operator transcription errors take place. The computation of a specific area is accomplished within the computer using the data transmitted from computer 10 and the analytical balance.

There is also provided an error free print-out by means of a spread sheet and word processor programs in the personal computer 10. The interface with Laboratory Information Management System (LIMS) 6 permits the automatic distribution via electronic mail to all eligible recipients of the analytical results, and the archiving of that information. Statistical process control is facilitated and corrective action expedited, since process drifts outside acceptable limits are monitored in real time.

All operator actions that might introduce bias have been removed. The only action required of the operator is to press the "R" (for RUN) key on the computer keyboard, and then press the "ENTER" key to start the analysis. This invention permits multi-point determinations of surface area, which simply involves the measurement of the volumes of adsorbate adsorbed at different relative pressures (gas mixtures) between 0.05 to 0.35.

Self-contained solenoid valves within the instrument are selected by keyboard commands from the personal computer. The data obtained at three different relative pressures is used by software programs to compute the multi-point surface area of the sample. The operator is then freed for other tasks within the laboratory during the measurement.

While only one embodiment of the present invention has been shown and described, it is to be understood that many changes and modifications may be made thereunto, without departing from the spirit and scope of the invention as defined in the appended claims.

What is claimed is:

1. In a method for determining the surface area of a material with a surface area analyzer which uses the dynamic flow method by continuously passing a stream of a gaseous mixture of known and constant composition consisting of an adsorbate nitrogen, and an inert gaseous diluent helium in contact at a constant pressure with a measured sample of the material on a once-through basis at a temperature at which neither the inert diluent nor the adsorbate is appreciably adsorbed by the sample, then while continuing said stream, cooling the sample to a temperature at which adsorption of the adsorbate by the sample selectively takes place by immersing the sample in a liquid bath, using a detector sensing means in a bridge configuration to continuously measure the decrease in the concentration of the adsorbate in the stream down stream of the sample, during the cooling and until equilibrium is re-established integrating the sensed signal from the sensing means using an integrating means to provide a signal that is proportional to the volume of gas adsorbed by the sample of the material and using the detector sensing means, sensing the decrease in concentration of the adsorbate over the period of cooling until equilibrium is re-established, the improvement comprising the steps of:

inhibiting by means of a gate all signals emanating from the detector sensing means immediately after the sample is cooled to its adsorption temperature, to eliminate false or phantom signals generated in the detector sensing means caused by the chilling of the gas mixture;

deactivating the inhibit gate to reconnect the detector sensing means to said integrating means, so that the return to equilibrium which signals the completion of absorption, can be detected;

removing the liquid nitrogen bath from the sample of material in response to the absorption completion signal to cause the sample of material to warm to ambient temperature, to permit desorption of the adsorbed nitrogen in the sample of material;

detecting the desorbed nitrogen from the sample of material using the detector sensing means to generate a signal proportional to the volume of nitrogen adsorbed by the sample of material; and integrating the desorption signal from said sensing means using the integrating means to provide a measure of the surface area of the sample of material.

2. The method as recited in claim 1, additionally comprising the step of automatically measuring the unbalance or drift of said detector sensing means, using an autozeroing circuit, and canceling said unbalance of said sensing means before beginning the integration of the desorption signal.

3. The method as recited in claim 2, wherein said step of canceling comprises providing a cancellation signal equal to the drift of said sensing means to a differential amplifier means which is coupled to the input of said integrating means.

4. The method as recited in claim 3, additionally comprising sequence gate means connected to the input of said integrating means for sending the completion of the signals detected by said sensing means, said sequence gate means having its output coupled to said autozeroing circuit for automatically canceling the drift of said sensing means at the completion of each signal sensed by said sensing means.

5. The method as recited in claim 4, additionally comprising the step of calibrating the bridge configured sensing means by injecting a known volume of adsorbate into the stream of gaseous mixture using an injection valve coupled to the gaseous stream for injecting a known volume of adsorbate gas into the stream.

6. The method as recited in claim 5, wherein following said step of calibrating, said sequence gate means automatically initiates the beginning of the adsorption cycle by cooling the sample of material, during completion of adsorption, warming the sample to initiate desorption, integrating the desorption signal, and computing the resultant surface area.

7. The method as recited in claim 6, additionally comprising interfacing said surface area analyzer to a computer at the output of said integrating means, said computer initiating the steps of measurement, said computer receiving the measurement signals and computing the surface area of the sample of material, and storing the data of each analysis performed.

8. The method as recited in claim 7, wherein said detector sensing means comprises a wheatstone bridge having thermal conductivity detecting elements located in the gaseous stream.

9. The method as recited in claim 5, additionally comprising a lift motor for raising a coolant to contact the sample of material, said lift motor being responsive to said sequence gate means for operating said lift motor following said step of calibration.

10. The method as recited in claim 9, comprising lowering the coolant using said lift motor in response to said sequence gate following completion of the adsorption cycle.

* * * * *